United States Patent [19]
Yakshin et al.

[11] 4,067,231
[45] Jan. 10, 1978

[54] DEVICE FOR MEASURING PARAMETERS OF IMPACT PULSES

[76] Inventors: Alexandr Sergeevich Yakshin, ulitsa Malaya Filevskaya 66, kv. 104; Oleg Nikolaevich Novikov, ulitsa Kuznetsky most 18/7, kv. 6; Dmitry Alexeevich Grechinsky, ulitsa Tolbukhina 8, korpus 2, kv. 48; Viktor Alexandrovich Klochko, ulitsa Oktyabrskaya 38, kv. 374; Viktor Georgievich Rygalin, 3 Dorozhny proezd, 5, korpus 2, kv. 103, all of Moscow, U.S.S.R.

[21] Appl. No.: 746,296

[22] Filed: Dec. 1, 1976

[51] Int. Cl.$^2$ ............................................... G01P 15/00
[52] U.S. Cl. ........................................ 73/658; 364/556
[58] Field of Search ................... 73/71.2, 71.4, 516 R, 73/517 R; 235/151.3

[56] References Cited

U.S. PATENT DOCUMENTS

| | | | |
|---|---|---|---|
| 3,455,149 | 7/1969 | Foster et al. | 73/71.4 |
| 3,930,248 | 12/1975 | Keller | 235/151.3 X |

*Primary Examiner*—James J. Gill
*Attorney, Agent, or Firm*—Lackenbach, Lilling & Siegel

[57] ABSTRACT

A device for measuring parameters of impact pulses comprises an acceleration pickup which converts mechanical vibrations of an object being studied into electrical signals, said electrical signals being supplied through an amplification unit to a means for measuring the impact speed variation.

12 Claims, 4 Drawing Figures

DEVICE FOR MEASURING PARAMETERS OF IMPACT PULSES

This invention relates to devices for measuring parameters of impact pulses and, in particular, to devices for measuring variations of impact speed in objects subjected to impact overload tests.

Impact processes research is one of the currently central problems involving estimation of various objects subjected to various types of impact loads resulting in internal stresses, strains, structural ruptures and shifts in the material of tested objects.

To evaluate the influence of an impact it is essential that energy characteristics of the dynamic action on tested objects are known and that, primarily, variations of impact speed of objects are also known.

Measurement of this parameter permits the investigation of plasto-elastic properties of the colliding objects, as well as the properties of impact tested objects. This helps to issue recommendations on designing shock stands and to select conditions of such tests.

Until recently parameters of impact pulses were measured by means of analogue equipment ensuring measurement of the peak value of an impact pulse. The impact pulse was at the same time registered by a light-beam oscillograph or photographed from the screen of an electron-beam oscillograph possessing long afterglow.

Other information required for evaluation of energy characteristics of the dynamic action on tested objects is obtained by deciphering and processing the recorded oscillograms of the impact pulse, which significantly reduces the delivery of information and makes timely correction of tests difficult, particularly when dealing with new materials and designs, and does not provide for high accuracy of measurements of the impact pulse parameters.

There is also known a digital device for measuring impact pulse parameters comprising an amplification unit, a filter and a device for measuring impact pulse parameters.

The means for measuring impact pulse parameters in said device is made up of coarse and fine comparators, some of their inputs being connected to the output of the input filter and other inputs being connected to the output of the digital-analogue converter. The outputs of the comparators and the input of the digital-analogue converter are coupled via a unit of a logical converter and lower and upper level digital registers.

Such design of the known device raised the accuracy of measurements of the peak value of an impact pulse, but said device's functional capabilities are limited, because it does not provide for evaluation of energy characteristics of dynamic action, particularly impact speed variations, which is an important parameter in studying impact processes.

There is known a device for measuring impact pulse parameters, wherein an acceleration pickup converts mechanical vibrations of the object being tested into electrical signals which are delivered via an amplification unit to a means for measuring impact speed. This means measures the peak value of an impact pulse and its duration, which provide information on total energy of the impact pulse.

The means for measuring the impact speed of said device comprises generally a memory unit, a control unit, an impact pulse level and duration detector, switches, an analogue-to-digital converter, a memory unit of the peak value of an impact pulse, a duration memory unit, a generator and a data register.

The means for impact speed measuring of the known device is given for one measuring channel, but the process of measurement is effected through three channels and the impact pulse duration memory unit stores time during which the signals of the impact pulse were higher than the threshold level.

The means for impact speed measuring converts analogue signals into digital ones, stores said signals and records in the impact pulse peak value data register the duration of the impact pulse and the period of time from the moment when the signal of the first channel became higher than the threshold value until the moment when the last channel produced a signal lower than the threshold value. This data is used to determine the energy characteristics of the impact.

Said device measures parameters of an impact pulse with a rather low accuracy and, moreover, determination of the impact speed variation requires deciphering of the output code, whereas information on impact speed variation is obtained by calculations.

It is an object of this invention to provide a device for measuring with high accuracy variations of the impact speed of objects subjected to impact action, which is a significant parameter for investigation of properties of these objects.

This is achieved by a device for measuring impact pulse parameters, wherein an acceleration pickup converts mechanical vibrations of a tested object into electrical signals which are supplied through an amplification unit to a means for measuring impact speed variations. According the invention, said means for measuring impact speed variations comprises an integrator input of said integrator being coupled to the output of the amplification unit, a first zero element equipped with a first reference voltage source connected to a second imput of said first zero element, said first input of said first zero element being connected to the output of said amplification unit, a first switch, an input of said first switch being connected to an output of the first zero element and an output of said first switch being connected to a second input of the integrator, so that the switch permits passage of the input signal from the amplification unit to the first input of the integrator when it is supplied a signal from the first zero organ, a leading pulse edge shaper and a first trailing pulse edge shaper, their inputs being connected to the output of the first zero organ, a first flip-flop and a second flip-flop, their first inputs being connected to the outputs of the leading and trailing pulse edge shapers respectively, an output of the first flip-flop being coupled to the third input of the integrator, so that it ensures putting the integrator out of the zero state for the time of passage of the input signal from the amplification unit to the first input of the integrator, a second switch, an input of said second switch being connected to an inverting output of the second flip-flop and an output of said second switch being connected to a fourth input of the integrator, so that it ensures connection of a second reference voltage source to the fourth input of the integrator, which polarity is opposite to the polarity of the input signal, a reset pulse shaper, an input of said reset pulse shaper being connected to the output of the leading pulse edge shaper, a second zero element connected to an output of the integrator, a second trailing pulse edge shaper whose input is connected to the output of the second zero element and whose output is connected to the second inputs of the first and second flip-flops and to an input of a transcription pulse shaper, and a digital indicator of the impact speed variation value equipped with the following series-connected elements high-frequency pulse generator, a third switch, whose second other input is connected to the output of the second flip-flop, a meter, whose reset line is connected to the output of the reset pulse shaper, a memory register, whose inputs are connected to the outputs of the meter and whose transcription line is connected to the output of the transcription pulse shaper, and an indicator display connected to the outputs of the memory register and serving to determine the value of the impact speed variation.

Such design of the device, according to the invention, a high accuracy measurement of the impact speed of objects subjected to impact action.

The invention will now be described in greater detail with reference to a specific embodiment thereof, taken in conjunction with the accompanying drawings, wherein.

Figure 1:
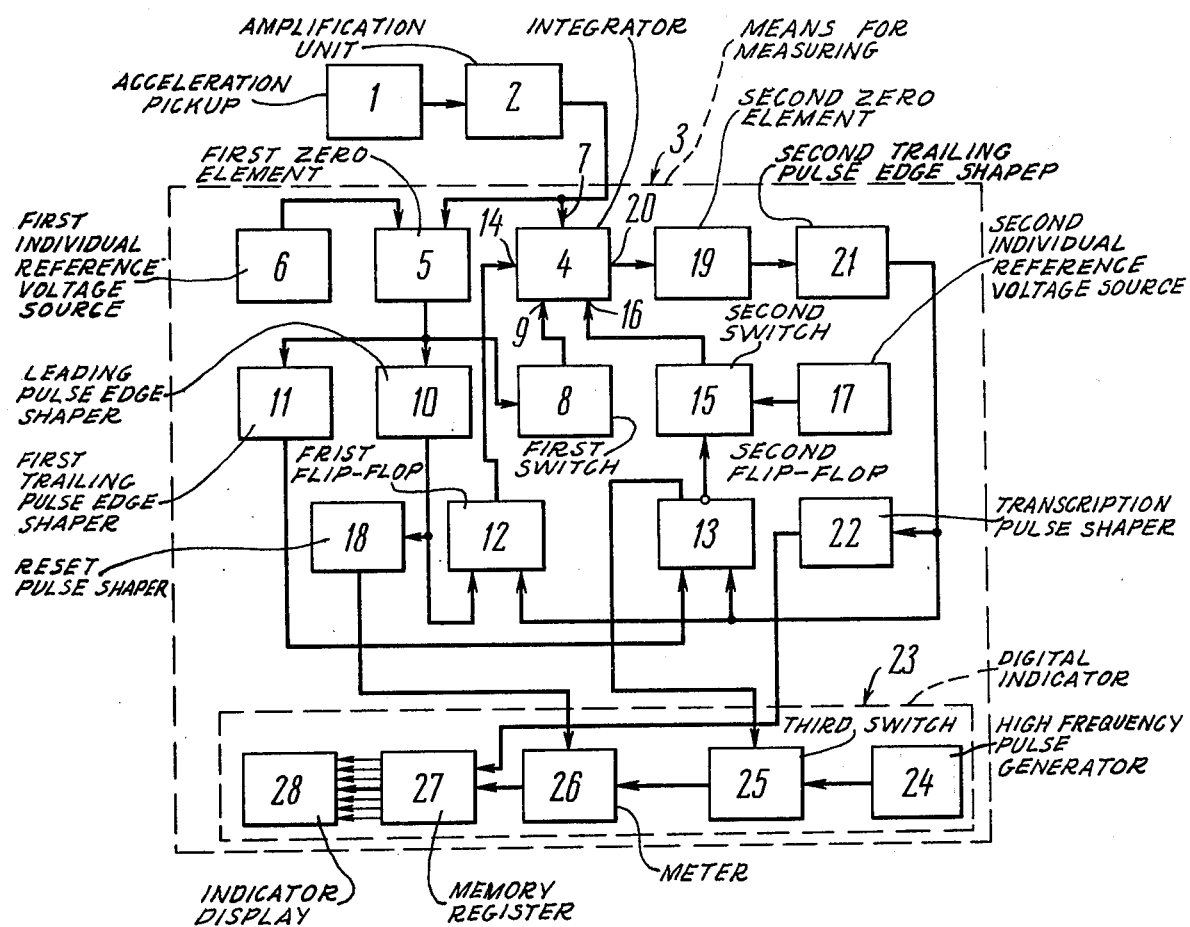
FIG. 1 shows a block diagram of a device for measuring parameters of impact pulses, according to the invention.

A device for measuring impact pulses parameters as shown in FIG. 1, comprises, according to the invention, an acceleration pickup 1 which converts mechanical vibrations of the tested object into electrical signals, a description of which can be found in many publications (cf. for example, V. S. Pellinets, "Measurement of Impact Accelerations", published by Standard, Moscow, 1975, pp. 184–190). Said acceleration pickup 1 is connected via an amplification unit 2 (described in the same book, pp. 191–204) to a means 3 for measuring variations of the impact speed, which is one of the parameters of the impact pulse.

The means 3 for measuring variations of the impact speed comprises an integrator 4 and a first zero element 5 equipped with a first individual reference voltage source 6. A first input 7 of the integrator 4 and a first input of the first zero element 5 are joined in a common input and are connected to the output of the amplification unit 2. The first reference voltage source 6 is connected to the second input of the first zero element 5.

The means 3 also comprises a first switch 8, whose input is connected to the output of the first zero element 5 and whose output is connected to a second input 9 of the integrator 4 so that the first switch 8 permits passage of the input signal from the amplification unit 2 to the first input 7 of the integrator 4 when a signal is applied to the first switch from the first zero organ 5, and a leading pulse edge shaper 10 and a first trailing pulse edge shaper 11 whose inputs are connected to the output of the first zero element 5 and whose outputs are connected to a first input of a first flip-flop 12 and a second flip-flop 13, respectively.

The output of the first flip-flop 12 is connected to a third input 14 of the integrator 4 so that it ensures putting the integrator 4 out of the zero state for the time of passage of the input signal from the amplification unit 2 to the first input 7 of the integrator 4. The inverting output of the second flip-flop 13 is connected to the input of the second switch 15, whose output is connected to a fourth input 16 of the integrator 4, so that it ensures connection of the second individual reference voltage source 17 to the fourth input 16 of the integrator 4, the polarity of the second reference voltage source 17 being opposite to the polarity of the input signal.

In addition, the means 3 for measuring variation of the impact speed comprises a reset pulse shaper 18, whose input is connected to the output of the leading pulse edge shaper 10; a second zero element 19, whose input is connected to an output 20 of the integrator 4; and a second trailing pulse edge shaper 21 whose input is connected to an output of the second zero element 19 and whose output is connected to the second inputs of the second flip-flop 13 and the first flip-flop 12 and to the input of a transcription pulse shaper 22.

The means 3 also comprises a digital indicator 23 of the value of variation of the impact speed having a first, a second and a third input. This indicator 23 comprises the following elements connected in series: a high frequency pulse generator 24; a third switch 25, which is connected by a second input, which is the first input of the means 23, to the output of the second flip-flop 13; and a meter 26, whose reset line, which is the second input of the means 23, is connected to the output of the reset pulse shaper 18 and whose outputs are connected to the inputs of a memory register 27. The transcription line of the memory register 27, which the third input of the means 23, is connected to the output of the transcription pulse shaper 22 and the outputs of said memory register 27 are connected to an indicator display 28, which serves to indicate the value of variation of the impact speed.

The functional diagram of the means 3 (FIG. 2) for measuring variation of the impact speed comprises, according to the invention, a first zero element 5 built with a microcircuit 29. The output of the microcircuit 29 is connected to a two-stage signal former, which includes transistors 30 and 31 with base resistors 32 and 33 and collector resistors 34 and 35 respectively. The collector resistor 35 of the transistor 31 is connected to the first switch 8. The first switch 8 includes transistors 36 and 37 with base resistors 38 and 39 and collector resistors 40 and 41. The collectors of the transistors 36 and 37 are connected to the resistors 42 and 43, their common outlet being coupled to the base of the transistor 44, whose collector is coupled to a zero potential line. A resistor 45 serves to select the mode of operation of the transistor 37.

In addition, the collector of the transistor 31 of the zero element 5 is connected to the leading pulse edge shaper 10 and to the first trailing pulse edge shaper 11.

The leading pulse edge shaper 10 is built around a transistor 46 and resistors 47 and 48.

The first trailing pulse edge shaper 11 is built with two transistors 49 and 50 and resistors 51, 52, 53, 54. The output of the leading pulse edge shaper 10 is coupled to the first R-input of the first flip-flop 12 and to the input of the reset pulse shaper 18. The output of the first trailing pulse edge shaper 11 is coupled to the first R-input of the second flip-flop 13.

The emitter of the transistor 44 of the switch 8 is connected to the center point of resistors 55 and 56 of the integrator 4. One end of the resistor 55 is connected to a noninverting input 57 of the microcircuit 29 and one end of the resistor 56 is connected to the inverting input of a microcircuit 58 of the integrator 4, whose other input is connected via a resistor 59 to the zero potential line. The output of the microcircuit 58 is connected via a capacitor 60 to the inverting input of the microcircuit 58 and via a resistor 61 to the emitter of a transistor 62, which forms together with transistors 63 and 64 and resistors 65, 66, 67, 68, 69, 70 and 71 the switch circuit of the integrator 4. The common point of the resistors 65 and 66 is connected to the inverting output of the flip-flop 12. The common point of the resistor 56, the capacitor 60, the inverting input of the microcircuit 58 and the resistor 61 is connected via a resistor 72 to the emitter of a transistor 73 of the second switch 15, the base of said transistor 73 being connected via a resistor 74 to the inverting output of the flip-flop 13.

The emitter of the transistor 73 of the second switch 15 is connected to the second reference voltage source 17 which comprises resistors 75,76 and a stabilitron 77.

The output of the microcircuit 58 of the integrator 4 is also connected to the noninverting input of a microcircuit 78, whose inverting input is connected to the zero potential line. The output of the microcircuit 78 is connected to a voltage divider built with resistors 79 and 80, whose central tap is connected to the emitter of the transistor 62 of the switch circuit of the integrator 4 and to the resistor 61.

The output of the microcircuit 58, which is the output 20 of the integrator 4, is connected to the input of the second zero element 19, the output 20 of the integrator 4 being connected via a resistor 81 to the noninverting input of the microcircuit 82 of the second zero element 19, whose other input is connected to a bias source comprising resistors 83, 84 and 85. The output of the microcircuit 82 of the second zero element 19 is connected to a two-stage signal shaper built with transistors 86 and 87, base resistors 88 and 89 and collector resistors 90, 91.

The collector of the transistor 87 of the second zero element 19 is connected via a capacitor 92 to the base of a transistor 93, which is the first stage of the two-stage second trailing pulse edge shaper 21. This shaper 21, apart from the transistor 93 and the capacitor 92, comprises a transistor 94, base resistors 95, 96 and collector resistors 97,98 respectively. The collector of the transistor 94 of the second trailing pulse edge shaper 21 is connected to the S-inputs of the flip-flops 13 and 12, as well as to a base resistor 99 of a transistor 100 of the transcription pulse shaper 22, the collector of the transistor 100 including a resistor 101.

The collector of the transistor 46 of the leading pulse edge shaper 10 is connected to the first R-input of the flip-flop 12 and to a base resistor 102 of a transistor 103 of the reset pulse shaper 18.

The reset pulse shaper 18, apart from the transistor 103 and the base resistor 102, comprises a transistor 104 with a base resistor 105 and collector resistors 106 and 107 of the transistors 103 and 104 respectively.

The S-inputs of the flip-flops 12 and 13 are connected to a manual zero setting line 108.

The means 3 for measuring the impact speed variation is provided with a digital indicator 23 (FIG. 3), which comprises the high frequency pulse generator 24 built with NAND elements 109, 110 and 111 embraced by feedbacks, the output of the first NAND element 109 being connected to the input of the second NAND element 110, an output of the NAND element 110 being connected to the input of the third NAND element 111 and a capacitor 112, which forms together with a resistor 113 the frequency-controlling RC circuit of the generator 24.

The resistor 113 is connected to the input of the first NAND element 109, which is connected to the output of the third NAND element 111. The common point of the resistor 113 and the input of the first NAND element 109 as the output of the high frequency pulse generator 24 and is connected to the second input of the third switch 25, which includes an element AND and whose first input is connected to the noninverting output of the flip-flop 13.

The output of the switch 25 is connected to the input of the meter 26. The meter 26 is built of four D-flip-flops 114, 115, 116 and 117 and two AND elements 118 and 119.

The D-input of the first D-flip-flop 114 is connected to its inverting output and to the C-input of the second D-flip-flop 115 and of the fourth D-flip-flop 117. The C-input of the first D-flip-flop 114 is connected to the output of the AND element of the switch 25. The R-inputs of all the D-flip-flops are joined and connected via a reset line to the output of the reset pulse shaper 18. The D-input of the second D-flip-flop 115 is connected to the output of the AND element 118, the inverting output of the D-flip-flop 115 is connected to the second input of the AND element 118 and the C-input of the third D-flip-flop 116, whose inverting output is connected to its D-input. The first input of the AND element 118 is connected to the inverting output of the fourth D-flip-flop 117, whose D-input is connected to the output of the AND element 119. The outputs of the second D-flip-flop 115 and the fourth D-flip-flop 117 are connected to the first and second inputs of the AND element 119 respectively. In addition, the outputs of the D-flip-flops 114, 115, 116 and 117 are connected to the D-inputs of D-flip-flops 120, 121, 122 and 123 of the memory register 27 respectively. The R-inputs of the D-flip-flops 120, 121, 122 and 123 are joined and connected via the transcription line to the transcription pulse shaper 22.

Figure 3:
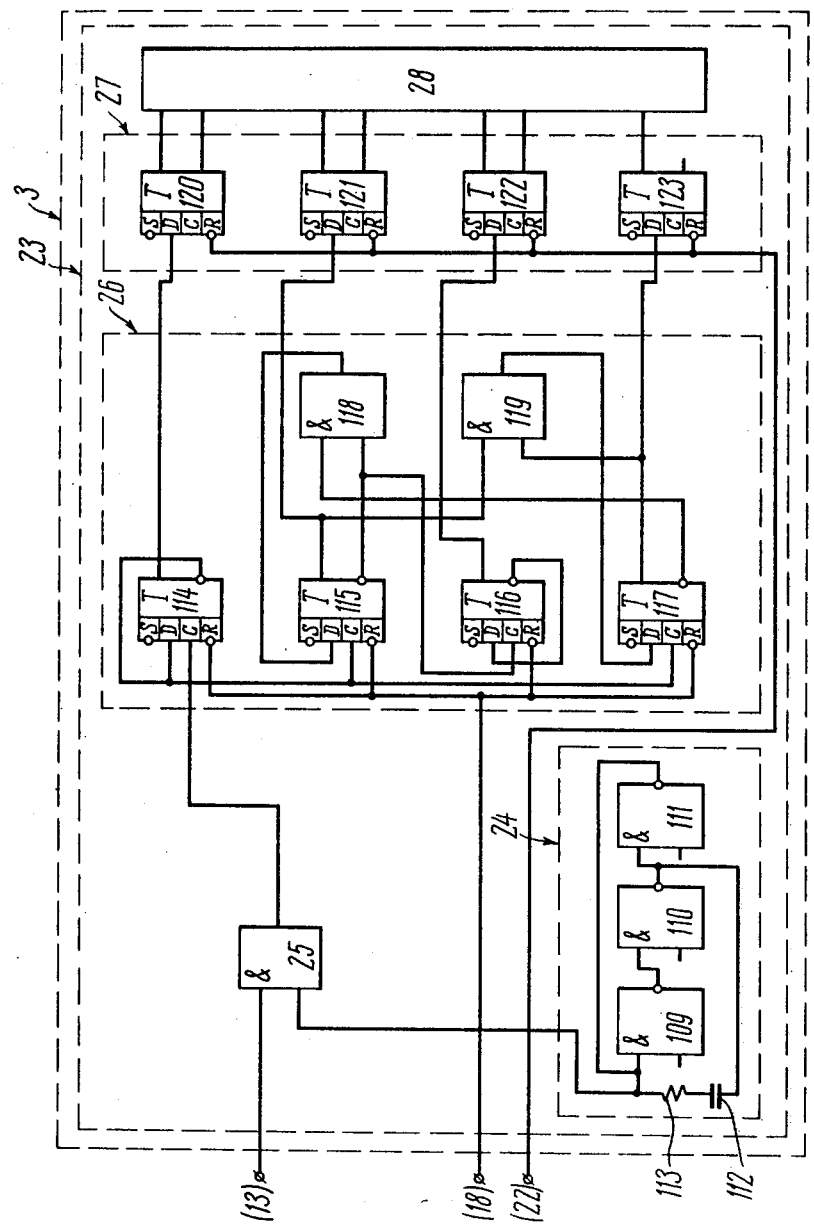
FIG. 3 shows a functional diagram of the digital indicator of the value of the impact speed variation of the means for measuring, according to the invention.

FIG. 3 shows a key diagram of one order of the meter 26 and one order of the memory register 27.

The operation of counting decades of orders of the meter 26 can be found in publications (cf. for example, L. M. Goldenberg "Pulse and Digital Devices", Svyaz publishers, Moscow, 1973, pp. 446–462).

The outputs of the D-flip-flops 120, 121, 122 and 123 are connected to the indicator display (cf. same book, pp. 462–467).

Figure 4:
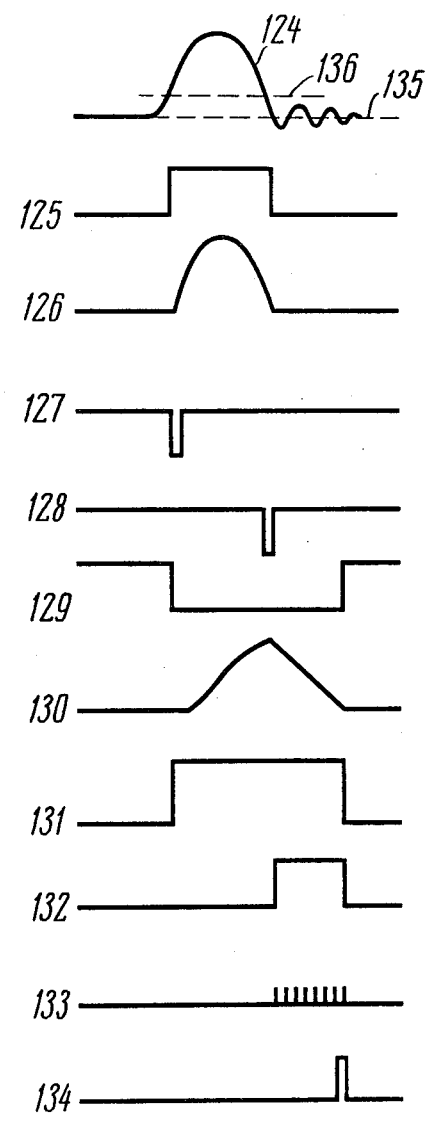
FIG. 4 shows geometric-time diagrams explanatory of the operation of the means for measuring impact speed variation, according to the invention.

For a better understanding of the principle of operation of the device for measuring impact pulse parameters, according to the invention, FIG. 4 is provided.

FIG. 4 shows an impact pulse 124, whose shape represents the mechanical shock affecting the tested object; a rectangular pulse 125 at the output of the first zero element 5; a signal voltage 126 at the output of the first switch 8; a pulse 127 at the output of the leading pulse edge shaper 10; a pulse 128 at the output of the first trailing pulse edge shaper 11; a pulse 129 at the output of the first flip-flop 12; a signal voltage 130 at the output of the integrator 4; a pulse 131 at the output of the second zero element 19; a pulse 132 at the output of the second flip-flop 13; counting pulses 133; a transcription pulse 134; a zero potential level 135 and a response level 136 of the zero element 5.

The device for measuring impact pulse parameters operates as follows.

When a mechanical shock is produced, a pulse signal appears at the output of the acceleration pickup 1 (FIG. 1) positioned on the tested object.

This pulse electrical signal is supplied to the amplification unit 2, which matches the output resistance of the acceleration pickup 1 with the input resistance of the following amplification stages, filters the signal to exclude high-frequency components of the pulsed signal, which distort the shape of the impact pulse, and amplifies it to the value required for further processing of the input signal. The impact pulse 124 (FIG. 4) whose shape represents the mechanical shock acting on the tested object is then supplied to the means 3 (FIG. 1) for measuring impact speed variation.

The pulse signal of negative polarity is fed to one input of the first zero element 5 and to the input 7 of the integrator 4.

The second input of the zero organ 5 is connected to the reference voltage source 6. The reference voltage source 6 is a direct current source and can be built with stabilitrons, for example (cf. for example, V. S. Pellinets, "Measurement of Impact Accelerations", Standard publishers, Moscow, 1975, p. 207).

Figure 2:
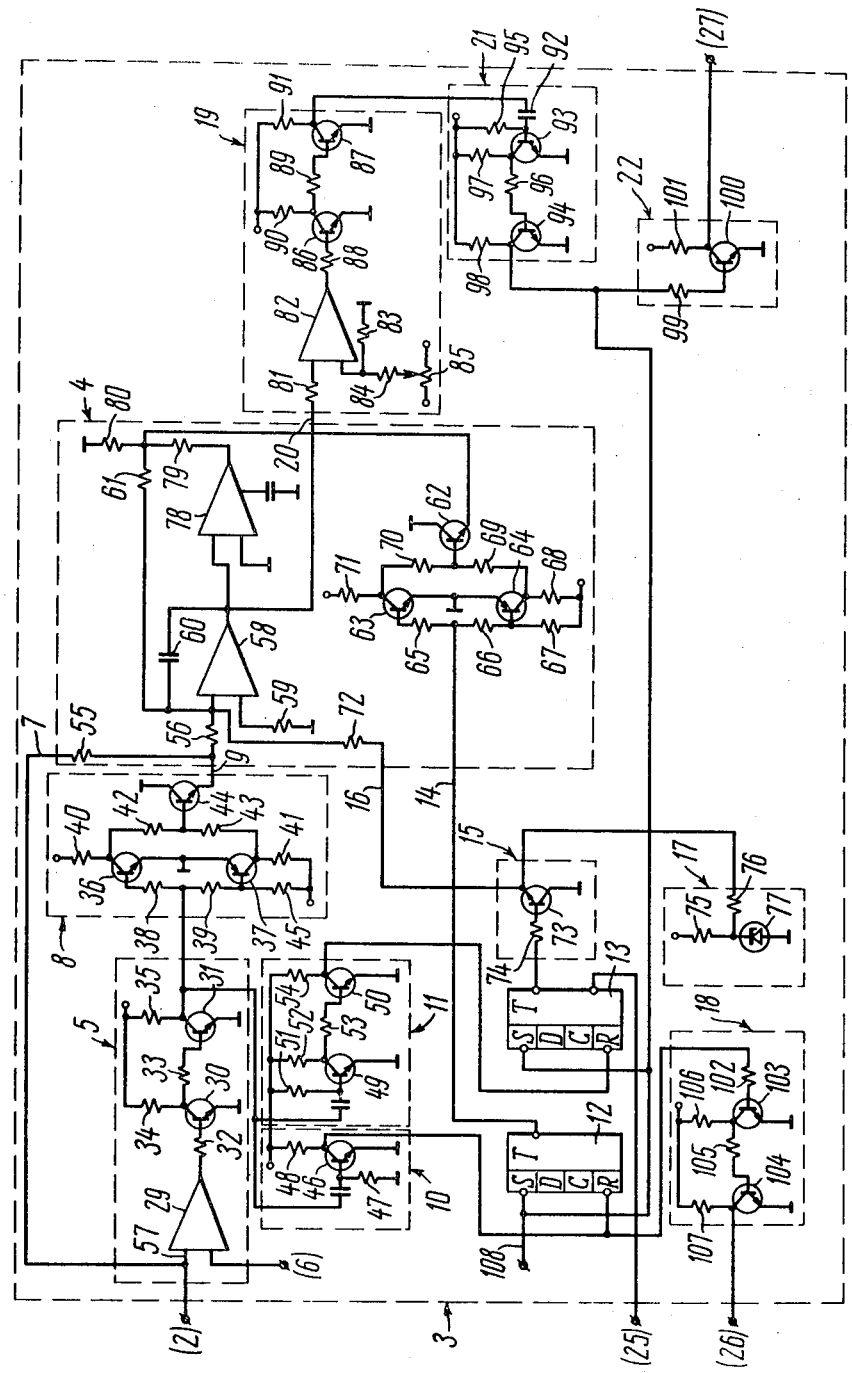
FIG. 2 shows a function diagram of a means for measuring the impact speed variation without the digital indicator, according to the invention.

The rectangular pulse 125 (FIG. 4) with a duration is formed at the output of the zero organ 5 depending on the value of voltage of the reference voltage source 6, which determines the response level 136 (FIG. 4) of the zero element 5, by the shaper built with the transistors 30 and 31 (FIG. 2). The pulse signal is supplied from the collector of the transistor 31 (FIG. 2) of the zero element 5 to the first switch 8 and to the leading pulse edge shaper 10 and the first trailing pulse edge shaper 11. The first switch 8 permits passage of the signal from the output of the amplification unit 2 to the input 7 of the integrator 4. The switch 8 is built with the transistors 36 and 37, which are of opposite polarities, and a switch element with a low residual voltage built with the transistor 44.

The positive potential from the collector of the transistor 31 of the zero element 5 opens the transistor 36 and closes the transistor 37. The negative potential from the collector loads using the resistors 42 and 43 closes the transistor 44, cutting off the input of the integrator 4 from the zero potential line and thus permitting passage of the input signal from the amplification unit 2 via the input 7 to the noninverting input of the microcircuit 58 of the integrator 4. In this case the voltage of the signal 126 is formed at the output of the first switch 8, which duration is equal to the duration of the rectangular pulse 125 at the output of the first zero element 5. The leading pluse edge shaper 10 forms the pulse 127 of the leading edge of the pulse 125 at the output of the zero organ 5, whereas the first trailing pulse edge shaper 11 forms the pulse 128 by the trailing edge of the pulse 125. The pulse 127 supplied from the output of the leading pulse edge shaper 10 sets the first flip-flop 12 and the pulse 129 from the output of the flip-flop 12 acts on the switch stages using the transistors 62, 63, 64 of the integrator 4 and closes the transistor 63 and opens the transistor 64. The transistor 62 in this case cuts off the feedback keeping the zero potential at the output of the integrator 4.

At the same time the reset pulse shaper 18 (FIG. 1) resets all flip-flops of the meter 26 of the digital indicator 23.

The measuring signal of the impact pulse begins being fed to the input 7 (FIG. 2) of the integrator 4 from the output of the amplification unit 2.

Operation of the integrator 4 can be found in more detail in the Author's Certificate No. 469,125, USSR, Cl. 06g 7/18.

The voltage 130 (FIG. 4) grows at the output of the integrator 4 proportional by to the integral of the input voltage during the duration of the rectangular pulse 125 at the output of the zero element 5 (FIG. 2). When the switch stages using the transistors 62, 63, 64 of the integrator 4 are cut off, the signal voltage 130 is supplied from the output of the microcircuit 58 via the output 20 of the integrator 4 to the input of the second zero element 19. The second zeroelement 19 starts shaping the pulse 131.

The pulse 128 fed from the output of the first trailing pulse edge shaper 11 sets the second flip-flop 13 and the voltage pulse fed from the inverting output of said flip-flop 13 closes the transistor 73 of the switch 15, thus permitting passage of the voltage from the reference voltage source 17 via the switch 15 to the input 16 of the integrator 4.

This voltage fed from the reference voltage source 17 has the polarity opposite to the polarity of the voltage of the input measuring signal of the impact pulse supplied to the input 7 of the integrator 4.

The switch 8 cuts off the input 7 of the integrator 4 from the amplification unit 2. At the same time the pulse signal 132 (FIG. 4) of the opposite polarity is supplied from the noninverting output of the second flip-flop 13 to the switch 25 (FIG. 3) of the digital indicator 23 using the AND element. In this case the switch 25 opens and the counting pulses 133 start arriving from the high frequency pulse generator 24 to the C-input of the D-flip-flop 114 of the meter 26.

The generator 24 using the NAND elements 109, 110 and 111 ensures stable operation at the expense of feedbacks embracing the NAND elements 109, 110 and 111. The frequency controlling RC-circuit composed of the resistor 113 and the capacitor 112 is connected to the input of the NAND element 109 and the output of the NAND element 110.

While the pulse is fed from the output of the second flip-flop 13 (FIGS. 1 and 2) to the input of the switch 15, the voltage 130 at the output of the integrator 4 decreases to the response level 136 of the zero element 5. As soon as the voltage at the output of the integrator 4 reaches the response level 136 of the zero element 5, the second zero element 19 operates and the second shaper 21 forms a pulse at the output of the zero element 19 of the trailing edge of the pulse 131. Said pulse is fed to the second inputs of the flip-flops 12 and 13 and sets them. At this moment the counting pulses 133 stop being fed to the meter 26 of the digital indicator 23, the switch 8 returns to the initial state, and the transistor 73 (FIG. 2) of the switch 25 opens and the switch 15 stops supply of the reference voltage from the reference voltage source 17 to the input 16 of the integrator 4. The trailing pulse edge shaper 21 feeds a pulse to the transcription pulse shaper 22 and the transcription pulse 134 is formed at its output (FIG. 4). The pulse 134 sends commands to the memory register 27 (FIG. 1) to record the results accumulated in the meter 26 and the indicator display indicates the value of impact speed variations of the tested object when acted upon by the impact pulse.

Employment of the claimed device for measuring impact pulse parameters permits prompt information on the total variation of the impact speed of the object and the shock stand platform, when impact loads are reproduced, or information on total variation of impact speed of two objects, one of them being the tested object. The total variation of the impact speed is the quantity which characterizes the energy state of the tested object as a result of impact action and knowing this parameter permits an investigation of the plasto-elastic properties of the tested objects, as well as preparation of recommendations for designing shock stands and selection of conditions for such tests.

What is claimed is:

1. A device for measuring parameters of impact pulses comprising:

an acceleration pickup having an output and which converts mechanical vibrations of the tested object into electrical signals;

an amplification unit having an input and an output, said input being connected to said output of said acceleration pickup; and a means for measuring the impact speed variation having an input and being connected by said input to said output of said amplification unit, said means for measuring includes an integrator having a first, a second, a third and a fourth input and an output and being connected by said first input to said output of said amplification unit; a first zero element having a first input, which is joined with said first input of said integrator and serves as said input of said means for measuring, a second input and an output; a first reference voltage source having an output and being connected by said output to the second input of the first zero element; a first switch having an input and an output being connected by its input to said output of the first zero element and by its output to said second input of said integrator so that the first switch permits passage of the input signal from said amplification unit to said first input of said integrator when a signal is fed to said first switch from the first zero element; a leading pulse edge shaper having an input and an output and being connected by its input to said output of the first zero element; a first flip-flop having a first and a second input and an output and being connected by its first input to said output of said leading pulse edge shaper and by its output to said third input of said integrator so that it ensures putting the integrator out of the zero state during the time of passage of the input signal from said amplification unit to said integrator; a first trailing pulse edge shaper having an input and an output and being connected by its input to said output of the first zero element; a second flip-flop having a first and a second input, and output, and an inverting output and being connected by its first input to said output of said first trailing pulse edge shaper; a second switch having an input and an output and being connected by its input to said inverting output of the second flip-flop; a second reference voltage source, whose polarity is opposite to the polarity of said input signal of said integrator, having an output; said second switch having its output connected to said fourth input of said integrator so that it ensures connection of said output of said second reference voltage source to said fourth input of said integrator; a reset pulse shaper having an input and an output and being connected by its input to said output of said leading pulse edge shaper; a second zero element having an input and an output and being connected by its input to said output of said integrator; a second trailing pulse edge shaper having an input and an output and being connected by its input to said output of said second zero element and by its output to the second inputs of the first and second flip-flops; a transcription pulse shaper having an input and an output and being connected by its input to said output of said second trailing pulse edge shaper; and a digital indicator of the value of the impact speed variation having a first, a second and a third input and being connected by its first input to said output of the second flip-flop, by its second input to said output of said reset pulse shaper and by its third input to said output of said transcription pulse shaper.

2. The device according to claim 1, wherein the digital indicator includes: a high frequency pulse generator having an output; a third switch having a first input, a second input and an output, said first input being connected to said output of said high frequency pulse generator, and said second input serving as said first input of said digital indicator; a meter having an input, a reset line and an output, said input being connected to said output of said third switch, and said reset line serving as said second input of said digital indicator; a memory register having an input, a transcription line and outputs, said input being connected to said output of said meter, and said transcription line serving as said third input of said digital indicator; and an indicator display having inputs connected to said outputs of said memory register, said indicator display indicating the value of the variations of the impact speed.

3. The device according to claim 1, wherein the first zero element includes: a microcircuit having a noninverting input, an inverting input and an output, said noninverting input being said first input of said first zero device, said inverting input being said second input of said first zero device; and a two-stage signal former including a first and a second transistor, a base resistor of said first transistor connecting the output of said microcircuit and the base of said first transistor, a base resistor of said second transistor connecting the collector of said first transistor and the base of said second transistor, collector resistors of each transistors being connected together, the collector of said second transistor being said output of said first zero element.

4. The device according to claim 1, wherein said first switch includes: a first transistor having a base resistor and a collector resistor, said base resistor being said input of said first switch; a second transistor having a base resistor and a collector resistor, said base resistor being connected to said base resistor of said first transistor and serving as said input of said switch, the emitters of said first and said second transistors being connected together; a resistor connecting said base of said second transistor and said collector resistor of said second transistor; and a third transistor, the base being connected to said collector resistor of said first transistor and to said collector resistor of said second transistor, the emitter of said third transistor being said output of said first switch.

5. The device according to claim 1, wherein said leading pulse edge shaper includes: a transistor, the collector being said output of said leading pulse edge shaper; a capacitor connected to the base of said transistor, said capacitor being said input of said leading pulse edge shaper; a first resistor connected to the base of said transistor; and a second resistor connected to the collector of said transistor.

6. The device according to claim 1, wherein said first trailing pulse edge shaper includes: a first transistor having a collector resistor; a capacitor connected to the base of said first transistor and being said input of said first trailing pulse edge shaper; a first resistor connecting the base of said first transistor and said collector resistor of said first transistor; a second transistor having a base resistor and a collector resistor, said base resistor being connected to the collector of said first transistor, the collector of said transistor being said output of said first trailing pulse edge shaper.

7. The device according to claim 1, wherein said second switch includes a transistor, the collector being said output of said second switch; and a base resistor being the input of said second switch.

8. The device according to claim 1, wherein said reset pulse shaper includes a first transistor having a base resistor and a collector resistor, said base resistor being said input of said reset pulse shaper; and a second transistor having a base resistor and a collector resistor, said base resistor being connected to the collector of said first transistor, the collector of said transistor being said output of said reset pulse shaper.

9. The device according to claim 1, wherein said second zero element includes a microcircuit having a non-inverting input, an inverting input and an output; a first resistor connected to said non-inverting input of said microcircuit and being said input of said second zero element; a bias source connected to said inverting input of said microcircuit; a first transistor having a base resistor and a collector resistor, said base resistor being connected to said output of said microcircuit; and a second transistor having a base resistor and a collector resistor, said base resistor being connected to the collector of said first transistor, the collector of said second transistor being said output of said second zero element.

10. The device according to claim 1, wherein said second trailing pulse edge shaper includes: a first transistor having a collector resistor; a capacitor connected to the base of said first transistor and being said input of said second trailing pulse edge shaper; a first resistor connecting the base of said first transistor and said collector resistor of said first transistor; a second transistor having a base resistor and a collector resistor, said base resistor being connected to the collector of said first transistor, the collector of said transistor being said output of said second trailing pulse edge shaper.

11. The device according to claim 1, wherein said transcription pulse shaper includes a transistor, the collector being said output of said transcription pulse shaper; a base resistor being said input of said transcription pulse shaper; and a collector resistor.

12. The device according to claim 1, wherein said integrator includes: a first microcircuit having an inverting input, a non-inverting input and an output, said output being said output of said integrator; a first resistor connected to said non-inverting input of said first microcircuit; a second resistor connected to said inverting input of said first microcircuit and being said second input of said integrator; a third resistor connected to said second resistor and being said first input of said integrator; a capacitor connecting said output and said inverting input of said first microcircuit; a fourth resistor connected to said inverting input of said first microcircuit and being said fourth input of said integrator; a second microcircuit having a non-inverting input, an inverting input and an output, said non-inverting input being connected to said output of said first microcircuit; a fifth resistor connected to said output of said second microcircuit; a sixth resistor connecting said fifth resistor and said inverting input of said first microcircuit; a first transistor, the emitter being connected to said fifth resistor; a second transistor having a base resistor and a collector resistor, said base resistor being said third input of said integrator; a seventh resistor connecting the base of said first transistor and the collector of said second transistor; an eighth resistor connecting said collector resistor of said second transistor and the base of said second transistor; a third transistor having a base resistor and a collector resistor, the base resistor being said third input of said integrator, the emitter of said third transistor being connected to the emitter of said second transistor; and a ninth resistor connecting the base of said first transistor and the collector of said second transistor.

* * * * *